United States Patent [19]
Merovitz et al.

[11] Patent Number: 5,881,387
[45] Date of Patent: Mar. 16, 1999

[54] SURGEON'S GLOVES FROM NEOPRENE COPOLYMERS

[75] Inventors: Gerald Merovitz, Florence, S.C.; Randy Tuck, Eaton, Ohio; Jim Burns, Plainsboro, N.J.; Russ Culp, Dothan, Ala.

[73] Assignee: Allegiance Corporation

[21] Appl. No.: 785,167

[22] Filed: Jan. 13, 1997

Related U.S. Application Data

[62] Division of Ser. No. 485,767, Jun. 7, 1995, abandoned.

[51] Int. Cl.$^6$ ............................... A41D 19/00; C08L 11/02
[52] U.S. Cl. ........................... 2/161.7; 604/292; 524/552; 524/569
[58] Field of Search ............................... 604/292; 2/161.7; 524/552, 569; 428/36.8

[56] References Cited

U.S. PATENT DOCUMENTS

| | | |
|---|---|---|
| 1,965,396 | 7/1934 | Stevens et al. . |
| 2,941,257 | 6/1960 | Davis . |
| 3,286,011 | 11/1966 | Kavali et al. . |
| 3,411,982 | 11/1968 | Kavali et al. . |
| 5,007,919 | 4/1991 | Silva et al. . |

FOREIGN PATENT DOCUMENTS 0 574 160A1  5/1993  European Pat. Off. .

OTHER PUBLICATIONS duPont Bulletin A Selection Guide For Neoprene Latexes, C.H. Gilbert, 1985.

duPont Bulletin Neoprene Latex Based Adhesives, D.G. Coe, 1993.

duPont Bulletin Neoprene Latexes–Their Preparation And Characteristics, L.L. Harrell, Jr. 1981.

Paper Nature Rubber Dipping Technologies, R.D. Culp et al., University of Maryland, 1989.

Paper Neoprene Latexes And Their Applications, F. McMillian ACS Toronoto, Canada 1991.

Paper Neoprene Latex And Its Applications With Emphasis On Manufacture Of Dipped Goods, C.H. Gilbert et al., ACS Montreal, 1987.

Dupont Bulletin A Selection Guide For Neoprene Latexes, C.H. Gilbert, 1985.

duPont Technical Bulletin NL–310.1 entitled "Basic Compounding Of Neoprene Latex".

duPont Technical Bulletin entitled "Compounding Neoprene Latex For Colloidal Properties".

*Primary Examiner*—Fred Teskin
*Attorney, Agent, or Firm*—Andrea Wayda; Kay Hannafan

[57] ABSTRACT

Certain neoprene copolymers make it possible to manufacture surgeon's gloves and Swanz-Ganz balloons having improved properties.

3 Claims, No Drawings

SURGEON'S GLOVES FROM NEOPRENE COPOLYMERS

This is a divisional of application Ser. No. 08/485,767 filed Jun. 7, 1995 now abandoned.

FIELD OF THE INVENTION

The invention relates to improved surgeon's gloves and compositions used in their manufacture.

BACKGROUND OF THE INVENTION

In some cases, natural rubber medical gloves may produce allergic responses in individuals predisposed to developing an allergic reaction to latex. Some of the medical literature has suggested that allergen response is especially high in rubber glove use in areas of medicine due to continuous exposure by healthcare providers. Resistance to changing from natural latex has always been associated with the uncomfortable, or different feel, of all other synthetic offerings; including neoprene, silicones and other type materials.

Neoprene surgical gloves now on the market generally are unpopular since they feel tight and inflexible on the hands of the user. Surgical users of these products prefer the soft and flexible tactility of a natural rubber glove. The neoprene compound, and process developed by this invention produces a synthetic glove that has a modulus lower than the prior art. The invention produces a neoprene glove of equal or better softness in feel to the common surgeon's glove constructed of natural latex.

ADVANTAGES OF THE INVENTION

The neoprene gloves of the invention are made of synthetic elastomers, yet they possess the look and feel of natural latex gloves. They are basically non-allergenic and are free of proteins. They may be made using existing glove manufacturing techniques and processes. The gloves of the invention are resistant to solvents and ozone. The gloves may be treated with conventional lubricant powders. Alternatively, the gloves may be powder-free while yet maintaining good mold release and donning properties. To acheive this effect, conventional halogenation procesis may be employed. There physical properties are not materially reduced after being subjected to radiation sterilization.

THE INVENTION

The invention comprises soft surgeon's glove or industrial medical gloves which have been constructed from a copolymer latex of neoprene and 2,3-dichloro-1,3- butadiene which copolymer contains between 25–55% and preferably, 35–45% of chlorine. In a most preferred embodiment, the copolymer contains 40% chlorine. The soft surgeon's glove may be further characterized as having a low modulus, a slow crystallization rate, a high wet gel strength and a medium gel content.

The invention also comprises compositions useful in producing the soft surgeon's gloves of the types described above. A general formula used in the preparation of the gloves is set forth below in Table 1.

TABLE 1

| INGREDIENTS | PARTS PER HUNDRED OF RUBBER |
|---|---|
| Neoprene Copolymer Latex | 100.00 |
| Plasticizer/Stabilizer | 0.25 to 10.00 |
| Emulsifier/Stabilizer | 0.25 to 10.00 |
| Antiozonant/Plasticizer | 0.25 to 10.00 |
| pH Stabilizer Sequestrate | 0.10 to 1.50 |
| pH Stabilizer | 0.10 to 1.50 |
| Vulcanization Activator | 0.25 to 20.00 |
| Crosslinker | 0.10 to 3.00 |
| Vulcanization Accelerator | 0.25 to 4.00 |
| Antioxidant | 0.10 to 3.00 |
| White Pigment* | 0.05 to 3.00 |
| Yellow Pigment* | 0.05 to 3.00 |
| (Rubber Reoderant) | 0.001 to 1.0 |
| Wetting Agent/Emulsifier | 0.001 to 1.0 |
| Defoamer | 0.001 to 2.0 |
| Rubber Softener | 0.0 to 50.0 |

*Optional Ingredients

DETAILED DESCRIPTION OF THE INVENTION

The Neoprene Copolymer Latex

As indicated, this copolymer of 2-chloro-1,3-butadiene and 2,3-dichloro, 3-butadiene contains between 30–50%, preferably 35–45% of chlorine and most preferably 40%. The modulus (of elasticity) MPa of these polymers should not be greater than 0.6 at 100%, preferably the modulus is about 0.4 at 100%. For a more detailed explanation of these values see Table II of the DuPont bulletin, A SELECTION GUIDE FOR NEOPRENE LATEXES, by C. H. Gilbert, 1985 (NL-020.1(R1)), which bulletin is incorporated herein by reference. These latexes may have a solids content ranging between 35–60% by weight. Preferably it is 50%. As indicated, the Copolymers useful in the practice of the invention have a slow crystallization rate, a medium gel content and a high wet gel strength. They are preferably anionic latexes. More information about these polymers is available by referring to the C. H. Gilbert Bulletin and the DuPont Bulletin, NEOPRENE LATEXES—THEIR PREPARATION AND CHARACTERISTICS, by L. L. Harrell Jr., 1981 (ADH 200.1). This reference is also incorporated herein by reference.

The preferred commercial latex used in the practice of the invention is made available by DuPont under the code number 750. This anionic copolymer latex has a chlorine content of 40% and possesses all of the preferred properties described above. Specific details describing this latex are to be found in the C. H. Gilbert Bulletin.

Glove Thickness

The term, "surgeon's glove," as used herein and in the claims includes related products such as examining gloves, fingers and Swanz-Ganz balloons on catheters for medical uses. It is an important feature of the invention that the gloves are thin gloves having an average thickness in any part of the glove less than 0.5". Preferably the thickness will not exceed 0.009". A typical glove produced in accordance with the invention has a cuff thickness of 0.006" and a finger thickness of 0.0075".

Processes for Making the Surgeon's Gloves

The gloves of the invention are preferably made using known dipping technologies. These processes are in most instances the well known processes e.g. straight dipping and coagulant dipping which latter process is most often comprises the Anode process or the Teague process. While either of these coagulation processes may be used in the practice of this invention the Anode process is most preferred. Descriptions of these processes are described in the publication, NATURAL RUBBER DIPPING TECHNOLOGIES, by R. D. Culp and B. L. Pugh, symposium on Latex as a Barrier Material Apr. 6 and 7 1989, University of Maryland. Another paper describing neoprene latex dipping is: NEOPRENE LATEX THEIR APPLICATIONS WITH EMPHASIS ON THE MANUFACTURE OF DIPPED GOODS, by O. H. Gilbert and H. E. Berkheimer, ACS spring Meeting, Rubber Division, Montreal, Quebec, May 27, 1987. These papers are incorporated herein by reference.

Yet another reference describing the dipping of neoprene latexes is the publication, NEOPRENE LATEXES AND THEIR APPLICATIONS, F. L. McMillan, ACS, Rubber Division, Toronto, Ontario, Canada, May 21–24, 1991. This Paper provides a good description of the various ingredients used in the formulation of neoprene latexes and their functions. This paper further provides a description of the Anode dipping process in the following language: "In the Anode process, a form is dipped into a coagulant, withdrawn, and rotated to allow uniform deposit of coagulant. After allowing it to dry partially, during which time the coagulant film becomes more viscous, the form is slowly and steadily dipped into the latex compound and held there for sufficient time to allow the film to build up to the desired thickness. It is then withdrawn at a steady rate—slowly enough to minimize flow of the outer layer of wet compound on the form." "As in straight dipping, rotation of the form after withdrawal helps to smooth out the film. The compound dip is often followed by another coagulant dip to set the wet film. Since the rate of buildup is very rapid at first but then decreases rapidly with dwell time and since the entire process can be repeated many times, it is often less expensive and faster to use multiple dips when producing heavy films."

Both of these latter two references are incorporated herein by reference.

EXAMPLES

Using an anode dipping process of the type described and a formula of the type shown in Table 1, surgeon's gloves were made and tested against commercial neoprene gloves. The results of these tests are set forth in Tables 2 and 3.

TABLE 2

| | SURGICAL GLOVES ORIGINAL | | | | | | | |
|---|---|---|---|---|---|---|---|---|
| | 500% MOD | ELONG | TENSILE | CUFF GAUGE | PALM GAUGE | FINGER GAUGE | WEIGHT | COLOR |
| COMMERCIAL GLOVE | 417 psi | 830% | 3365 psi | 0085 | 0077 | 0078 | 5 grams | GOLD |
| GLOVE* OF INVENTION | 255 psi | 1100 | 2595 psi | 0060 | 0085 | 0072 | 13 grams | YELLOW |

| ASTM STANDARDS | TYPE 1 (NATURAL) | TYPE 11 (SYNTHETIC) |
|---|---|---|
| 500% MODULUS | 800 PSI MAX | 1020 PSI MAX |
| ELONGATION | 750% MIN | 650% MIN |
| TENSILE | 3500 PSI MIN | 2470 PSI MIN |

*NOTE: GLOVES OF THE INVENTION WERE NOT STERILIZED

TABLE 3

| | SURGICAL GLOVES AFTER ACCELERATED AGING 158° F. — 7 DAYS | | | | | | | |
|---|---|---|---|---|---|---|---|---|
| | 500% MOD | ELONG | TENSILE | CUFF GAUGE | PALM GAUGE | FINGER GAUGE | WEIGHT | COLOR |
| COMMERCIAL GLOVE | 597 psi | 787% | 2890 psi | 0085 | 0077 | 0078 | 15 grams | GOLD |
| GLOVE* OF INVENTION | 255 psi | 933% | 3834 psi | 0060 | 0085 | 0072 | 13 grams | YELLOW |

| ASTM STANDARDS | TYPE 1 (NATURAL) | TYPE 11 (SYNTHETIC) |
|---|---|---|
| 500% MODULUS | NONE | NONE |
| ELONGATION | 560% MIN | 490% MIN |
| TENSILE | 2610 PSI MIN | 1740 PSI MIN |

*NOTE: GLOVES OF THE INVENTION WERE NOT STERILIZED

TABLE 4

To illustrate the fact that radiation sterilization does not materially diminish the physical properties of the gloves of the invention. Table 4 is set forth below.

PHYSICAL PROPERTIES

| TEST NO. | TEST AVERAGE OF NO. OF TESTS | PSI TINSLE | PSI MODULUS (STRESS) | % ELONGATION | 7-DAY PSI TINSLE | % ELONGATION |
|---|---|---|---|---|---|---|
| BEFORE STERILIZATION | | | | | | |
| 1. | 3 | 3,000 | 200 | 1,100 | 4,000 | 1,000 |
| 2. | 3 | 3,125 | 200 | 1,100+ | — | — |
| AFTER CONVENTIONAL STERILIZATION BY RADIATION | | | | | | |
| 3. | 5 | 3,500 | 225 | 1,080 | 3,600 | 880 |
| 4. | 5 | 2,600 | 200 | 1,100 | 2,825 | 850 |
| 5. | 5 | 2,550 | 250 | 1,090 | 2,900 | 820 |
| 6. | 5 | 2,700 | 200 | 1,090 | 2,925 | 850 |
| 7. | 5 | 3,500 | 200 | 1,090 | 3,900 | 850 |
| 8. | 5 | 3,650 | 200 | 1,090 | 3,600 | 900 |

Using a similar formula, Swanz-Ganz balloons were prepared. These balloons successfully passed standard pressure tests.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the claims appended hereto and their equivalents.

We claim:

1. A surgeon's glove comprising:
   100 parts copolymer latex of neoprene and 2,3-dichloro-1,3-butadiene latex wherein the copolymer latex contains between 25% to 55% by weight of chlorine;
   from 0.25 to 10.00 parts plasticizer/stabilizer;
   from 0.25 to 10.00 parts emulsifier/stabilizer;
   from 0.25 to 10.00 parts antiozonant/plasticizer;
   from 0.10 to 1.50 parts pH stabilizer sequestrant;
   from 0.10 to 1.50 parts pH stabilizer;
   from 0.25 to 20.00 parts vulcanization activator;
   from 0.10 to 3.00 parts crosslinker;
   from 0.25 to 4.00 parts vulcanization accelerator;
   from 0.10 to 3.00 parts antioxidant;
   from 0.001 to 1.00 parts rubber reoderant;
   from 0.001 to 1.00 parts wetting agent/emulsifier;
   from 0.001 to 2.00 parts defoamer; and
   from 0.00 to 50.0 parts rubber softener;
   wherein the glove has a 500% modulus of elasticity less than 417 p.s.i.

2. The soft surgeon's glove of claim 1 wherein the copolymer includes from 35% to 45% chlorine by weight.

3. The soft surgeon's glove of claim 1 wherein the copolymer includes 40% chlorine by weight.

* * * * *